(12) United States Patent
Wang (10) Patent No.: US 7,754,475 B2
(45) Date of Patent: Jul. 13, 2010

(54) NUCLEIC ACID PROBES AND MICROARRAYS FOR ANALYSIS OF POLYNUCLEOTIDES

(75) Inventor: Hui Wang, Cupertino, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 11/555,230

(22) Filed: Oct. 31, 2006

(65) Prior Publication Data

US 2007/0172845 A1 Jul. 26, 2007

Related U.S. Application Data

(60) Provisional application No. 60/762,294, filed on Jan. 25, 2006.

(51) Int. Cl.
*C12M 1/34* (2006.01)
*B01L 3/10* (2006.01)
*C12Q 1/68* (2006.01)

(52) U.S. Cl. .................. 435/287.2; 422/61; 435/6; 536/23.1; 536/24.3

(58) Field of Classification Search .......... 435/6, 435/287.2; 422/61; 536/23.1, 24.3
See application file for complete search history.

(56) References Cited

U.S. PATENT DOCUMENTS

| 5,556,752 | A | 9/1996 | Lockhart et al. | |
|---|---|---|---|---|
| 5,770,365 | A * | 6/1998 | Lane et al. | 435/6 |
| 6,355,423 | B1 | 3/2002 | Rothberg et al. | |
| 6,423,535 | B1 | 7/2002 | Arnold et al. | |
| 6,531,286 | B2 * | 3/2003 | Jayasena et al. | 435/6 |
| 6,660,480 | B2 * | 12/2003 | Ramsey et al. | 435/6 |
| 6,794,499 | B2 | 9/2004 | Wengel et al. | |
| 7,230,092 | B2 * | 6/2007 | Bortolin et al. | 435/6 |
| 2003/0003490 | A1 | 1/2003 | Fan et al. | |
| 2003/0022207 | A1 | 1/2003 | Balasubramanian et al. | |
| 2003/0165917 | A1 * | 9/2003 | Ullman et al. | 435/6 |
| 2005/0037362 | A1 | 2/2005 | Remacle et al. | |
| 2005/0266418 | A1 * | 12/2005 | Chen et al. | 435/6 |
| 2007/0003937 | A1 | 1/2007 | Wang | |
| 2007/0099193 | A1 | 5/2007 | Wang | |
| 2007/0172845 | A1 | 7/2007 | Wang | |

FOREIGN PATENT DOCUMENTS

| WO | WO 9401550 A1 * | 1/1994 |
|---|---|---|
| WO | WO0157248 A2 | 8/2001 |

(Continued)

OTHER PUBLICATIONS

Aravin et al. FEBS Letters 2005, vol. 579, pp. 5830-5840.*

(Continued)

*Primary Examiner*—Dave Nguyen
*Assistant Examiner*—Narayan K Bhat (57) ABSTRACT

The invention provides a probe for detecting a target polynucleotide. The probe contains a region that base-pairs with a target polynucleotide to form a duplex and a RNA hairpin extension domain that increases the stability of the duplex. The probe may further include a nucleotide clamp, a stem-complementary region and/or a linker moiety. Also provided is an array of subject probes bound to a surface of a solid support. Methods of using a subject probe to assess target polynucleotides, e.g., small RNAs, in a sample are provided, as are kits for use in practicing the subject methods.

17 Claims, 2 Drawing Sheets

FOREIGN PATENT DOCUMENTS

| | | |
|---|---|---|
| WO | WO2004078946 A2 | 9/2004 |
| WO | WO2004081520 A2 | 9/2004 |
| WO | WO2005003318 A2 | 1/2005 |
| WO | WO2005047301 A1 | 5/2005 |

OTHER PUBLICATIONS

Merriam—Webster dictionary brochure for definition, p. 1.*

Novina et al., "The RNAi revolution", Nature (2004) 430:161-64.

Liu et al., "An oligonuleotidfe microchip for genome-wide microRNA profiling in human and mouse tissues", Proc. Natl. Acad. Sci. (2004) 101:9740-44.

Thomson et al., "A custom microarray platform for analysis of microRNA gene expression", Nature Methods (2004) 1:47-53.

Babak et al., "Probing microRNAs with microarrays: Tissue specificity and functional inference", RNA (2004) 10:1813-19.

Walter et al., "Coaxial stacking of helixes enhances binding of oligoribonucleotides and improves predictions of RNA folding", Proc. Natl. Acad. Sci. (1994) 91:9218-22.

Ambros et al., "A uniform system for microRNA annotation", RNA (2003) 9:277-79.

Baskerville et al., "Microarray profiling of microRNAs reveals frequent coexpression with neighboring miRNAs and host genes", RNA (2005) 11:241-47.

Griffiths-Jones, "The microRNA Registry", Nucl. Acids Res. (2004) 32:D109-D111.

Riccelli, P.V., et al., Hybridization of single-stranded DNA targets to immobilized complementary DNA probes: comparsion of hairpin versus linear capture probes. Nucleic Acids Research. 2001, vol. 29, No. 4, pp. 996-1004.

* cited by examiner

NUCLEIC ACID PROBES AND MICROARRAYS FOR ANALYSIS OF POLYNUCLEOTIDES

RELATED APPLICATIONS

This application is a non-provisional application claiming priority to the provisional application Ser. No. 60/762,294 filed on Jan. 25, 2006 by Wang, entitled "External hairpin probe-target stabilization in miRNA microarrays".

BACKGROUND OF THE INVENTION

Since the discovery of the biological activity of short interfering RNAs (siRNAs) over a decade ago, so called "small RNAs" (i.e., short non-coding regulatory RNAs that have a defined sequence) have become a subject of intense interest in the research community. Exemplary short RNAs include siRNAs, microRNAs (miRNAs), tiny non-coding RNAs (tncRNAs) and small modulatory RNAs (smRNAs), as well as many others.

Although the exact biological functions of most small RNAs remain a mystery, it is clear that they are abundant in plants and animals. For example, to date, over 78 *Drosophila* microRNA species and 300 human microRNA species have been identified. The levels of the individual species of small RNA, in particular microRNA species, appear to vary according to the developmental stage and type of tissue being examined. It is thought that the levels of particular small RNAs may be correlated with particular phenotypes, as well as with the levels of particular mRNAs and proteins. Further, viral microRNAs have been identified, and their presence has been linked to viral latency.

Methods that provide for quantitative detection of small RNAs are therefore extremely valuable. To this end, a considerable amount of effort is currently being put into developing array platforms to facilitate the analysis of small RNAs, particularly microRNAs.

However, in order to perform array experiments that provide quantitative results, it is highly desirable to use an array that provides for specific binding to small RNAs. The design of arrays for the analysis of small RNAs is challenging because certain small RNAs are very short (e.g., in the range of 19-21 nucleotides in length), severely limiting the choices of sequences that can be employed in a probe for those small RNAs. Further, prior art small RNA detection methods may not discriminate between the small RNA and the precursor RNAs from which they are made, leading to results that do not accurately reflect the actual amount of a small RNA in a sample.

In view of the above, there is a great need for improved polynucleotide probes for assessing small RNAs in a sample. The invention described herein meets this need, and others.

Literature of Interest

Literature of interest includes: Novina et al., Nature (2004) 430:161-64; Liu et al., Proc. Natl. Acad. Sci. (2004) 101: 9740-44; Thomson et al., Nature Methods (2004) 1:1-7; Babak et al., RNA (2004) 10:1813-19; Pfeffer et al., Science (2004) 304:734-36; Nelson et al., Science (2001) 294:858-62; Liu et al., Nanobiology (1999) 4: 257-62; Walter et al., Proc. Natl. Acad. Sci. (1994) 91:9218-22; Ambros et al. RNA (2003) 9:277-79; Baskerville et al. RNA (2005) 11:241-47; and Griffiths-Jones, Nucl. Acids Res. (2004) 32:D109-D111.

SUMMARY OF THE INVENTION

The invention provides a probe for detecting a target polynucleotide, e.g., a small RNA, in a sample. The probe includes a target complementary region, a stem-complementary region, and a RNA hairpin extension domain. The RNA hairpin extension domain stabilizes binding of the target polynucleotide to the target complementary region. In certain embodiments, the RNA hairpin extension domain is covalently attached to the target complementary region via a nucleotide clamp region. Also provided is an array of subject probes bound to a surface of a solid support. Methods of using a subject probe to assess polynucleotides in a sample are provided, as are kits for use in practicing the subject methods. The invention finds use in a wide variety of diagnostic and research applications.

BRIEF DESCRIPTION OF THE FIGURES

These and other features of the invention will be understood from the description of representative embodiments of the method herein and the disclosure of illustrative apparatus for carrying out the method, taken together with the Figures, wherein FIG. 1 schematically illustrates an embodiment of the invention.

To facilitate understanding, identical reference numerals have been used, where practical, to designate corresponding elements that are common to the Figures. Figure components are not drawn to scale.

DETAILED DESCRIPTION

The term "nucleic acid" and "polynucleotide" are used interchangeably herein to describe a polymer of any length, e.g., greater than about 10 bases, greater than about 100 bases, greater than about 500 bases, greater than 1000 bases, usually up to about 10,000 or more bases composed of nucleotides, e.g., deoxyribonucleotides or ribonucleotides, or compounds produced synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides typically are referenced by the name or abbreviation of the nucleobase that forms part of their structure, including guanine, cytosine, adenine, thymine, and uracil (G, C, A, T, and U, respectively).

The terms "ribonucleic acid" and "RNA" as used herein mean a polymer composed of ribonucleotides. The terms "deoxyribonucleic acid" and "DNA" as used herein mean a polymer composed of deoxyribonucleotides. The term "oligonucleotide" as used herein denotes a single stranded multimer of nucleotides of from about 2 to 100 nucleotides. Oligonucleotides are usually synthetic and, in many embodiments, are up to about 60 nucleotides in length.

The term "oligomer" is used herein to indicate a chemical entity that contains a plurality of monomers. As used herein, the terms "oligomer" and "polymer" are used interchangeably, as it is generally, although not necessarily, smaller "polymers" that are prepared using the functionalized substrates of the invention, particularly in conjunction with combinatorial chemistry techniques. Examples of oligomers and polymers include polydeoxyribonucleotides (DNA), polyribonucleotides (RNA), other nucleic acids that are N- or C-glycosides of a purine or pyrimidine base, polypeptides (proteins), polysaccharides (starches, or polysugars), and other chemical entities that contain repeating units of like chemical structure.

The terms "nucleoside" and "nucleotide" are intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

The term "sample" as used herein relates to a material or mixture of materials, typically, although not necessarily, in fluid form, containing one or more components of interest.

The phrase "surface-bound nucleic acid" refers to a nucleic acid that is immobilized on a surface of a solid substrate, where the substrate can have a variety of configurations, e.g., a sheet, bead, or other structure. In certain embodiments, the nucleic acid probes employed herein are present on a surface of the same planar support, e.g., in the form of an array.

The term "analyte" is used herein to refer to a known or unknown component of a sample. In certain embodiments of the invention, an analyte may specifically bind to a capture agent on a support surface. In general, analytes are typically RNA or other polynucleotides. Typically, an "analyte" is referenced as a species in a mobile phase (e.g., fluid), to be detected by a "capture agent" which, in some embodiments, is bound to a support, or in other embodiments, is in solution. However, either of the "analyte" or "capture agent" may be the one which is to be evaluated by the other (thus, either one could be an unknown mixture of components of a sample, e.g., polynucleotides, to be evaluated by binding with the other). A "target" references an analyte. "Target RNA" references a RNA expected to be present in a sample being analyzed; a "target RNA" is an RNA for which there is at least one probe having a target complementary region directed to the target RNA. The target polynucleotide (e.g. target RNA) includes a particular nucleic acid sequence of interest. Thus, the "target" can exist in the presence of other nucleic acid molecules or within a larger nucleic acid molecule.

The term "capture agent" refers to an agent that binds an analyte through an interaction that is sufficient to permit the agent to bind and concentrate the analyte from a homogeneous mixture of different analytes. The binding interaction may be mediated by an affinity region of the capture agent. Representative capture agents include polypeptides and polynucleotides, for example antibodies, peptides, or fragments of double stranded or single-stranded DNA or RNA may employed. Capture agents usually "specifically bind" one or more analytes.

A "target complementary region" is generally a portion of a probe (e.g. on an array) that is intended to bind to a target during the hybridization assay, for example a target small RNA. The target complementary region generally contains a contiguous nucleotide sequence that is complementary to the nucleotide sequence of a corresponding target small RNA (e.g. target miRNA) and is of a length that is sufficient to provide specific binding between the probe and the corresponding small RNA. Since miRNAs are generally in the range of about 19 to about 25 nucleotides (nt) in length, in certain embodiments the target complementary region is generally at least about 10 nt, at least about 12 nt, or at least about 15 nt in length. In certain embodiments target complementary region may be as long as about 18 nt, as long as about 20 nt, as long as about 22 nt, or as long as about 25 nt in length, or longer. In certain embodiments, the target complementary region may be as long as about 30 nt, as long as about 40 nt, as long as about 50 nt, or longer. The target complementary region therefore is directed to (e.g. hybridizes to and may be used to detect) a particular target polynucleotide, e.g. a particular target RNA.

"Sequence" may refer to a particular sequence of bases and/or may also refer to a polynucleotide having the particular sequence of bases. Thus a sequence may be information or may refer to a molecular entity, as indicated by the context of the usage. A duplex is a double stranded structure typically formed between complementary nucleic acid sequences. An intermolecular duplex is a double stranded structure typically formed between two different polynucleotide molecules that have complementary nucleic acid sequences, wherein the complementary nucleic acid sequences are hybridized to each other. A "DNA/RNA duplex" includes complementary nucleic acid sequences from a DNA molecule and from a RNA molecule hybridized to each other. A "target/probe duplex" includes complementary nucleic acid sequences from a target polynucleotide and from probe hybridized to each other. A "stem-duplex" is a double stranded structure that includes a sequence from a stem complementary region and a complementary sequence from a RNA hairpin extension domain hybridized to each other to form a duplex.

"Complementary" references a property of specific binding between polynucleotides based on the sequences of the polynucleotides. As used herein, polynucleotides are complementary if they bind to each other in a hybridization assay under stringent conditions, e.g. if they produce a given or detectable level of signal in a hybridization assay. Portions of polynucleotides are complementary to each other if they follow conventional base-pairing rules, e.g. A pairs with T (or U) and G pairs with C. "Complementary" includes embodiments in which two polynucleotides are strictly complementary and also includes embodiments in which two polynucleotides are substantially complementary. In this regard, "strictly complementary" is a term used to characterize a first polynucleotide and a second polynucleotide, such as a target and a capture agent directed to the target, and means that every base in a sequence (or sub-sequence) of contiguous bases in the first polynucleotide has a corresponding complementary base in a corresponding sequence (or sub-sequence) of contiguous bases in the second polynucleotide. "Strictly complementary" means that there are no insertions, deletions, or substitutions in either of the first and second polynucleotides with respect to the other polynucleotide (over the complementary region). Put another way, every base of the complementary region may be paired with its complementary base, e.g. following normal base-pairing rules. "Substantially complementary" is a term used to characterize a first polynucleotide and a second polynucleotide, and means that there may be one or more relatively small (less than 10 bases, e.g. less than 5 bases, typically less than 3 bases, more typically a single base) insertions, deletions, or substitutions in the first and/or second polynucleotide (over the complementary region) relative to the other polynucleotide. The complementary region is the region that is complementary between a first polynucleotide and a second polynucleotide (e.g. a target analyte and a capture agent; further e.g. a small RNA and a small RNA binding site in a long polynucleotide such as a messenger RNA). Complementary sequences are typically embedded within larger polynucleotides, thus two relatively long polynucleotides may be complementary over only a portion of their total length. The complementary region is typically at least about 10 bases long, more typically at least about 12 bases long, more typically at least about 15 bases long, still more typically at least about 20 bases long, or may be at least about 25 bases long. In various typical embodiments, the complementary region may be up to about 200 bases long, or up to about 120 bases long, up to about 100 bases long, up to about 80 bases long, up to about 60 bases long, up to about 45 bases long, or up to about 40 bases long.

If a polynucleotide, e.g. a capture agent, is "directed to" a target, the polynucleotide has a sequence that is complementary to a sequence in that target and will specifically bind (e.g. hybridize) to that target under hybridization conditions. The hybridization conditions typically are selected to produce binding pairs of nucleic acids, e.g., capture agents and targets, of sufficient complementarity to provide for the desired level of specificity in the assay while being incompatible to the formation of binding pairs between binding members of insufficient complementarity to provide for the desired specificity. Such hybridization conditions are typically known in the art. Examples of such appropriate hybridization conditions are also disclosed herein for hybridization of a sample to an array. The target will typically be a small RNA, e.g. an miRNA, for embodiments discussed herein.

The phrase "labeled population of nucleic acids" refers to mixture of nucleic acids that are detectably labeled, e.g., fluorescently labeled, such that the presence of the nucleic acids can be detected by assessing the presence of the label.

The term "array" encompasses the term "microarray" and refers to an ordered array presented for binding to nucleic acids and the like.

An "array," includes any two-dimensional or substantially two-dimensional (as well as a three-dimensional) arrangement of spatially addressable regions bearing nucleic acids, particularly oligonucleotides or synthetic mimetics thereof, and the like, e.g., UNA oligonucleotides. Where the arrays are arrays of nucleic acids, the nucleic acids may be adsorbed, physisorbed, chemisorbed, or covalently attached to the arrays at any point or points along the nucleic acid chain.

Any given substrate may carry one, two, four or more arrays disposed on a surface of the substrate. Depending upon the use, any or all of the arrays may be the same or different from one another and each may contain multiple spots or features. A typical array may contain one or more, including more than two, more than ten, more than one hundred, more than one thousand, more ten thousand features, or even more than one hundred thousand features, in an area of less than 20 $cm^2$ or even less than 10 $cm^2$, e.g., less than about 5 $cm^2$, including less than about 1 $cm^2$, less than about 1 $mm^2$, e.g., 100 $\mu m^2$, or even smaller. For example, features may have widths (that is, diameter, for a round spot) in the range from a 10 $\mu m$ to 1.0 cm. In other embodiments each feature may have a width in the range of 1.0 $\mu m$ to 1.0 mm, usually 5.0 $\mu m$ to 500 $\mu m$, and more usually 10 $\mu m$ to 200 $\mu m$. Non-round features may have area ranges equivalent to that of circular features with the foregoing width (diameter) ranges. At least some, or all, of the features are of different compositions (for example, when any repeats of each feature composition are excluded the remaining features may account for at least 5%, 10%, 20%, 50%, 95%, 99% or 100% of the total number of features). Inter-feature areas will typically (but not essentially) be present which do not carry any nucleic acids (or other biopolymer or chemical moiety of a type of which the features are composed). Such inter-feature areas typically will be present where the arrays are formed by processes involving drop deposition of reagents but may not be present when, for example, photolithographic array fabrication processes are used. It will be appreciated though, that the inter-feature areas, when present, could be of various sizes and configurations.

Each array may cover an area of less than 200 $cm^2$, or even less than 50 $cm^2$, 5 $cm^2$, 1 $cm^2$, 0.5 $cm^2$, or 0.1 $cm^2$. In certain embodiments, the substrate carrying the one or more arrays will be shaped generally as a rectangular solid (although other shapes are possible), having a length of more than 4 mm and less than 150 mm, usually more than 4 mm and less than 80 mm, more usually less than 20 mm; a width of more than 4 mm and less than 150 mm, usually less than 80 mm and more usually less than 20 mm; and a thickness of more than 0.01 mm and less than 5.0 mm, usually more than 0.1 mm and less than 2 mm and more usually more than 0.2 and less than 1.5 mm, such as more than about 0.8 mm and less than about 1.2 mm. With arrays that are read by detecting fluorescence, the substrate may be of a material that emits low fluorescence upon illumination with the excitation light. Additionally in this situation, the substrate may be relatively transparent to reduce the absorption of the incident illuminating laser light and subsequent heating if the focused laser beam travels too slowly over a region. For example, the substrate may transmit at least 20%, or 50% (or even at least 70%, 90%, or 95%), of the illuminating light incident on the front as may be measured across the entire integrated spectrum of such illuminating light or alternatively at 532 nm or 633 nm.

Arrays can be fabricated using drop deposition from pulse-jets of either precursor units (such as nucleotide or amino acid monomers) in the case of in situ fabrication, or the previously obtained nucleic acid. Such methods are described in detail in, for example, the previously cited references including U.S. Pat. No. 6,242,266, U.S. Pat. No. 6,232,072, U.S. Pat. No. 6,180,351, U.S. Pat. No. 6,171,797, U.S. Pat. No. 6,323,043, U.S. patent application Ser. No. 09/302,898 filed Apr. 30, 1999 by Caren et al., and the references cited therein. As already mentioned, these references are incorporated herein by reference. Other drop deposition methods can be used for fabrication, as previously described herein. Also, instead of drop deposition methods, photolithographic array fabrication methods or any other known array fabrication methods may be used. Inter-feature areas need not be present particularly when the arrays are made by photolithographic methods as described in those patents.

An array is "addressable" when it has multiple regions of different moieties (e.g., different oligonucleotide sequences) such that a region (i.e., a "feature" or "spot" of the array) at a particular predetermined location (i.e., an "address") on the array will detect a particular sequence. Array features are typically, but need not be, separated by intervening spaces. In the case of an array in the context of the present application, the "population of labeled nucleic acids" or "labeled sample" and the like will be referenced as a moiety in a mobile phase (typically fluid), to be detected by "surface-bound nucleic acids" which are bound to the substrate at the various regions.

A "scan region" refers to a contiguous (typically rectangular) area in which the array spots or features of interest, as defined above, are found or detected. Where fluorescent labels are employed, the scan region is that portion of the total area illuminated from which the resulting fluorescence is detected and recorded. Where other detection protocols are employed, the scan region is that portion of the total area queried from which resulting signal is detected and recorded. For the purposes of this invention and with respect to fluorescent detection embodiments, the scan region includes the entire area of the slide scanned in each pass of the lens, between the first feature of interest, and the last feature of interest, even if there exist intervening areas that lack features of interest.

An "array layout" refers to one or more characteristics of the features, such as feature positioning on the substrate, one or more feature dimensions, and an indication of a moiety at a given location. "Hybridizing" and "binding", with respect to nucleic acids, are used interchangeably.

The term "stringent assay conditions" as used herein refers to conditions that are compatible to produce binding pairs of nucleic acids, e.g., probes and targets, of sufficient complementarity to provide for the desired level of specificity in the assay while being incompatible to the formation of binding pairs between binding members of insufficient complementarity to provide for the desired specificity. The term stringent assay conditions refers to the combination of hybridization and wash conditions.

A "stringent hybridization" and "stringent hybridization wash conditions" in the context of nucleic acid hybridization (e.g., as in array, Southern or Northern hybridizations) are sequence dependent, and are different under different experimental parameters. Exemplary stringent hybridization conditions that can be used to identify nucleic acids within the scope of the invention can include, e.g., hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. Hybridization buffers suitable for use in the methods described herein are well known in the art and may contain salt, buffer, detergent, chelating agents and other components at pre-determined concentrations.

The term "mixture", as used herein, refers to a combination of elements, that are interspersed and not in any particular order. A mixture is heterogeneous and not spatially separable into its different constituents. Examples of mixtures of elements include a number of different elements that are dissolved in the same aqueous solution, or a number of different elements attached to a solid support at random or in no particular order in which the different elements are not spacially distinct. In other words, a mixture is not addressable. To be specific, an array of surface-bound oligonucleotides, as is commonly known in the art and described below, is not a mixture of surface-bound oligonucleotides because the species of surface-bound oligonucleotides are spatially distinct and the array is addressable.

"Isolated" or "purified" generally refers to isolation of a substance (compound, polynucleotide, protein, polypeptide, polypeptide composition) such that the substance comprises a significant percent (e.g., greater than 1%, greater than 2%, greater than 5%, greater than 10%, greater than 20%, greater than 50%, or more, usually up to about 90%-100%) of the sample in which it resides. In certain embodiments, a substantially purified component comprises at least 50%, 80%-85%, or 90-95% of the sample. Techniques for purifying polynucleotides and polypeptides of interest are well-known in the art and include, for example, ion-exchange chromatography, affinity chromatography and sedimentation according to density. Generally, a substance is purified when it exists in a sample in an amount, relative to other components of the sample, that is not found naturally.

The terms "determining", "measuring", "evaluating", "assessing" and "assaying" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

The term "using" has its conventional meaning, and, as such, means employing, e.g., putting into service, a method or composition to attain an end. For example, if a program is used to create a file, a program is executed to make a file, the file usually being the output of the program. In another example, if a computer file is used, it is usually accessed, read, and the information stored in the file employed to attain an end. Similarly if a unique identifier, e.g., a barcode is used, the unique identifier is usually read to identify, for example, an object or file associated with the unique identifier.

If a subject nucleic acid probe "corresponds to" or is "for" a certain small RNA, the nucleic acid probe base pairs with, i.e., specifically hybridizes to, that small RNA. As will be discussed in greater detail below, a nucleic acid probe for a particular small RNA and the particular small RNA, or complement thereof, usually contain at least one region of contiguous nucleotides that is complementary in sequence.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Where a range of values is provided, it is understood that each intervening value, to the tenth of the unit of the lower limit unless the context clearly dictates otherwise, between the upper and lower limit of that range and any other stated or intervening value in that stated range is encompassed within the invention.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

Figure 1:
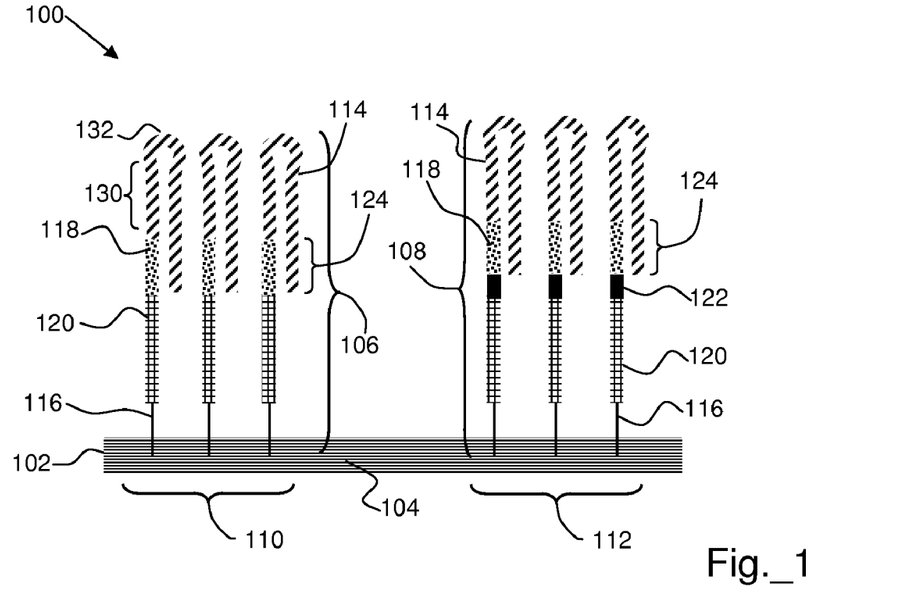

Accordingly, in particular embodiments, the present invention provides a probe for detecting a target polynucleotide, e.g., a small RNA, in a sample, as well as providing arrays having such probes. Referring now to FIG. 1, an embodiment of an array 100 in accordance with the invention is illustrated. The array 100 includes an array support 102 having a surface 104. Probes 106, 108 are bound to the surface 104 of the array support 102 to provide features 110, 112 of the array. The probes 106, 108 make up a set of probes bound to the surface 104. Each of the probes 106, 108 includes a RNA hairpin extension domain 114 and, optionally, a linker moiety 116. In particular embodiments, the probe is about 25 to about 150 nucleotides long, typically about 30 to about 100 nucleotides long, more typically about 35 to about 80 nucleotides long. The probe 106, 108 may be attached via its 3' end or its 5' end to the array support 102.

The RNA hairpin extension domain 114 is a RNA sequence configured to form a hairpin structure, wherein the hairpin structure includes a stem region 130 and a loop region 132. The hairpin structure typically has a loop region 132 of at least 3 or 4 nucleotides (typically up to about 8, 10 or 12 nucleotides) and a double-stranded stem region 130 (typically of about 4 to about 25 base pairs) in which complementary nucleotides bind to each other in an anti-parallel manner. In typical embodiments such as shown in FIG. 1, the RNA hairpin extension domain 114 also may include a sequence that is complementary to stem-complementary region 118 and forms a DNA/RNA duplex with stem-complementary region 118. The RNA hairpin extension domain 114 typically is at least 15 nucleotides long, e.g. at least 18, 20, 25, 30 nucleotides long. In typical embodiments, the RNA hairpin extension domain 114 typically is up to 50 nucleotides long, or longer, e.g. up to 60, 75, or 100 nucleotides long, though in some embodiments the RNA hairpin extension domain 114 may be longer.

The RNA hairpin extension domain 114 is typically bound to the surface 104 via the linker moiety 116, as shown in FIG. 1. The linker moiety 116 is optional; thus, in certain embodiments, the RNA hairpin extension domain 114 is bound to the surface 104 directly. The linker moiety, if present, is typically a polymer that does not interact or hybridize with the target RNAs in the sample. A suitable linker moiety may be, for example, about 5 to about 20 nucleotides long.

Each probe 106, 108 further includes a target complementary region 120 bound to the surface 104 via the optional linker moiety 116. Thus, the RNA hairpin extension domain 114 is bound to the surface 104 via the target complementary region 120 and the optional linker moiety 116 (if present). The target complementary region 120 is typically a DNA sequence that is complementary to a target RNA. In certain embodiments, such as illustrated at feature 112 of the array 100, the probes 108 include a nucleotide clamp region 122 between the RNA hairpin extension domain 114 and the target complementary region 120. The probes 106, 108 of a given feature 110, 112 typically all have the same target complementary region 120. The identity (sequence) of a target complementary region 120 will typically differ from feature to feature of the array, each feature 110, 112 of the array 100 having a different target complementary region 120. In typical embodiments, each of the target complementary regions is directed to a target RNA, e.g. a small RNA (such as a miRNA), and is capable of binding to its respective target RNA during a hybridization assay, e.g. when a sample containing small RNAs (including miRNAs) is contacted with the array under conditions sufficient to provide for specific binding, e.g. under stringent hybridization conditions. The sequences of the target complementary regions 120 are selected during the probe design process to be capable of base-pairing (e.g. during a hybridization assay) to a target RNA, e.g. to a particular small RNA (e.g. miRNA) of interest. The target complementary region 120 typically is at least 10 nucleotides long, e.g. at least 12, 15, 18, 20, 25 nucleotides long. In typical embodiments, the target complementary region 120 typically is up to 30 nucleotides long, or longer, e.g. up to 35, 40, 50, 60, 75, or 100 nucleotides long, though in some embodiments the target complementary region 120 may be longer.

In typical embodiments, the probes 106, 108 include a stem-complementary region 118 that is complementary to a portion of the RNA hairpin extension domain 114, as pictured in FIG. 1. The stem-complementary region 118 hybridizes to and forms a duplex 124 (denoted a "stem-duplex" herein) with the portion of the RNA hairpin extension domain 114. In certain embodiments the stem-complementary region 118 may be omitted; in such probes, the RNA hairpin extension domain 114 is bound to the surface 104 via the nucleotide clamp region 122 (if present), the target complementary region 120 and the optional linker moiety 116 (if present). The stem-complementary region 118 generally has the same sequence in all of the probes 106, 108 of the array 100, although in some embodiments the stem-complementary region 118 may be different in various probes 106, 108. The stem-complementary region 118 typically is a DNA sequence that is complementary to a portion of the RNA hairpin extension domain 114. In typical embodiments, the stem-complementary region 118 is directed to a portion of the RNA hairpin extension domain 114 and is capable of binding to said portion of the RNA hairpin extension domain during a hybridization assay, e.g. when a sample containing small RNAs is contacted with the array under conditions sufficient to provide for specific binding, e.g. under stringent hybridization conditions. The stem-complementary region 118 typically is at least 3 nucleotides long, e.g. at least 4, 5, 6, 8, 10, 12, 15 nucleotides long. In typical embodiments, the stem-complementary region 118 typically is up to 20 nucleotides long, or longer, e.g. up to 25, 30, 35, 40, or 50 nucleotides long, though in some embodiments the stem-complementary region 118 may be longer.

In certain embodiments, a probe 108 includes a nucleotide clamp 122 bound directly to the target complementary region 120. Thus, the nucleotide clamp 122 is bound to the surface 104 via the target complementary region 120 and the optional linker moiety 116 (if present), in that order. The nucleotide clamp 122 contains a contiguous sequence of up to about 5 nucleotides (i.e., 1, 2, 3, 4 or 5 nucleotides), wherein the identity of the nucleotides employed in the nucleotide clamp may be the same as each other or different from each other. The nucleotide clamp 122 typically contains nucleotides selected from G and C, possibly A, T, or U, or a modified nucleotide.

In typical embodiments, the elements of the probes (including the RNA hairpin extension domain 114, stem-complementary region 118, nucleotide clamp region 122, target complementary region 120, and linker moiety 116) are covalently attached in the order shown in the Figures or as otherwise described herein.

In certain embodiments of the invention a subject probe is a "surface-bound nucleic acid probe", where such a nucleic acid probe is bound, usually covalently but in certain embodiments non-covalently, to a surface of a solid substrate, i.e., a sheet, bead, or other structure. In certain embodiments, a surface-bound nucleic acid probe may be immobilized on a surface of a planar support, e.g., as part of an array.

In certain embodiments the array includes a set of probes 106, 108 which is made up of a plurality of sub-sets of probes, each subset corresponding to a different feature 110, 112, wherein every probe in a given subset has the same target complementary sequence 120, and different subsets of probes 106, 108 have different target complementary sequences 120.

In certain embodiments, the array includes other capture agents in addition to the probes disclosed herein; such other capture agents may be directed to control polynucleotides, analytes other than small RNAs, other transcripts, etc.

A subject array may contain a plurality of features (i.e., 2 or more, about 5 or more, about 10 or more, about 15 or more, about 20 or more, about 30 or more, about 50 or more, about 100 or more, about 200 or more, about 500 or more, about 1000 or more, usually up to about 10,000 or about 20,000 or more features, etc.), each containing a different probe for detecting a target RNA, e.g. a small RNA such as a miRNA. As few as one and as many as all of the features of a subject array may contain a probe having a RNA hairpin extension domain. In certain embodiments, at least 5%, at least 10% or at least 20% of the features of an array contain a probe having a RNA hairpin extension domain as described herein.

In many embodiments different probes are present in different features of an array, i.e., spatially addressable areas of an array. In many embodiments a single type of probe is present in each feature (i.e., all the nucleic acid probes in the feature have the same sequence). However, in certain embodiments, the probes in a feature may be a mixture of nucleic acids having different sequences.

A subject array may have a single probe such as is described herein. However, in more typical embodiments, a subject array may contain a plurality of subject probes that correspond to (and may be used to detect) a corresponding plurality of target polynucleotides (e.g. small RNAs). In particular embodiments, the subject arrays may contain probes for detecting at least a portion of all the identified small RNAs of a particular organism.

In general, methods for the preparation of nucleic acid arrays, particularly oligonucleotide arrays, are well known in the art (see, e.g., Harrington et al., Curr Opin Microbiol. (2000) 3:285-91, and Lipshutz et al., Nat Genet. (1999) 21:20-4) and need not be described in any great detail. The subject nucleic acid arrays can be fabricated using any means available, including drop deposition from pulse jets or from fluid-filled tips, etc, or using photolithographic means. Either polynucleotide precursor units (such as nucleotide monomers), in the case of in situ fabrication, or previously synthesized polynucleotides can be deposited. Such methods are described in detail in, for example U.S. Pat. Nos. 6,242,266, 6,232,072, 6,180,351, 6,171,797, 6,323,043, etc., the disclosures of which are herein incorporated by reference.

Figure 2:
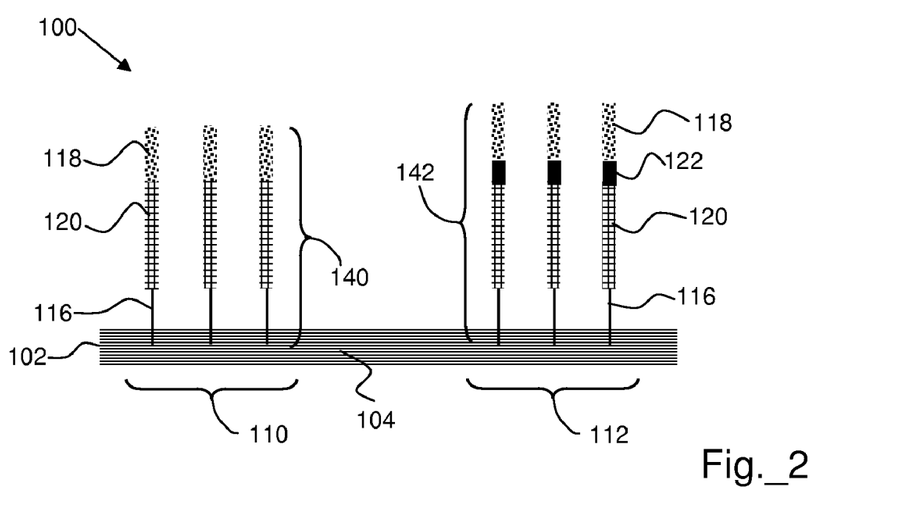
FIG. 2 schematically illustrates certain features of polynucleotides useful for some embodiments.
Figure 3:
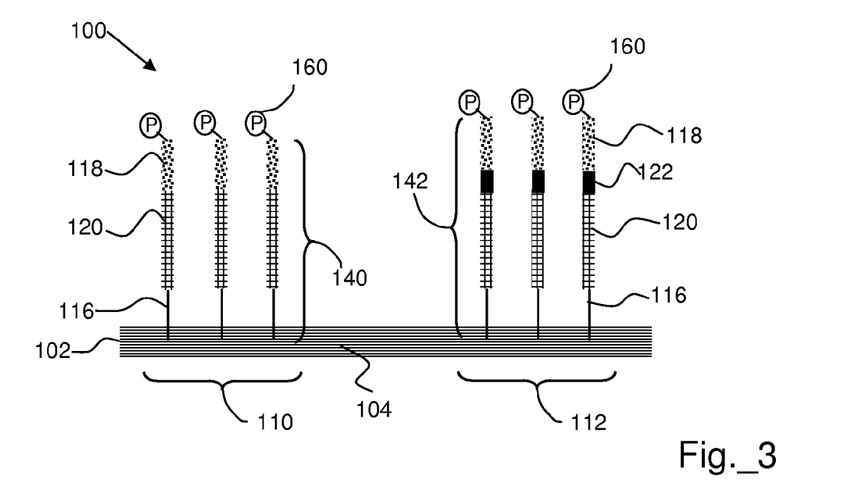
FIG. 3 schematically illustrates polynucleotides that have 5'-phosphate groups.

In certain embodiments, an array 100 such as shown in FIG. 2 is employed to provide the subject arrays. In FIG. 2, oligonucleotides 140 and 142 are disposed on a surface 104 of an array substrate 102 to form features 110, 112. Oligonucleotides 140 and 142 include stem-complementary region 118, target complementary region 120, and linker moiety 116. In addition, oligonucleotides 142 includes nucleotide clamp region 122. The array 100 as shown in FIG. 2 may be provided by any known method, including those described in the previous paragraph. In such embodiments for providing the subject arrays, the oligonucleotides 140, 142 are bound to the surface 104 at their 3' ends, and their 5' ends are distal from the substrate. The oligonucleotides 140, 142 are then phosphorylated using any known method, e.g. chemical or enzymatic method, to provide the 5'-phosphorylated oligonucleotides 140, 142 shown in FIG. 3. A typical method includes using T4 polynucleotide kinase or other enzyme having a 5'-phosphorylase activity. Alternatively, the array 100 with the 5'-phosphorylated oligonucleotides 140, 142 shown in FIG. 3 may be provided by any other known method, e.g. immobilization onto the substrate of oligonucleotides that already have 5'-phosphate groups. The 5'-phosphorylated oligonucleotides 140, 142 of FIG. 3 are then ligated to RNA hairpin oligonucleotides (which include a sequence that is complementary to the stem-complementary region 118) using T4 ligase. Exemplary conditions for the ligation reaction are described in Wang et al., Proc. Nat'l Acad. Sci. (1996) 93:9477-82. The RNA hairpin oligonucleotides typically hybridize to the stem-complementary region 118, and the T4 ligase enzyme then covalently attaches the RNA hairpin oligonucleotides to the oligonucleotides 140 and 142 to provide a subject array such as shown in FIG. 1. Thus, an oligonucleotide array such as that shown in FIG. 2 may be modified by the method here described (or any methods providing equivalent results) to provide subject arrays such as illustrated in FIG. 1.

Figure 4:
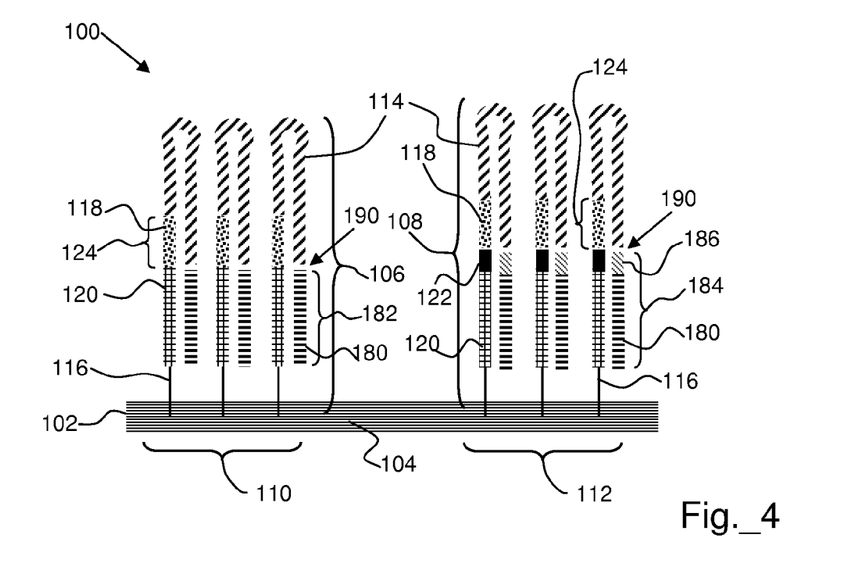
FIG. 4 schematically illustrates exemplary methods of the invention.

In an embodiment in accordance with the present invention, an array 100 such as that shown in FIG. 1 is employed in a method of performing an array analysis of an RNA sample that includes target RNAs, e.g. a sample that include small RNAs. In exemplary methods described herein, a sample containing target RNAs is contacted with the array 100 under conditions sufficient to provide for binding to the array. FIG. 4 shows an array 100 which has been contacted with a sample of target RNAs. Target complementary regions 120 are hybridized to target RNAs 180 from the RNA sample (forming target/probe duplexes 182, 184). The probes 106 disposed at the feature 110 specifically bind to a particular target RNA 180, e.g. a small RNA, and the probes disposed at the feature 112 specifically bind to a different target RNA 180, e.g. a different small RNA.

The target RNA 180 binds to the probes 106, 108 directly adjacent the RNA hairpin extension domain 114 such that the terminal nucleotides of the target RNA 180 and the RNA hairpin extension domain 114 are directly adjacent each other (indicated by arrow 190). The stem-complementary region 118 and the RNA hairpin extension domain 114 form a DNA/RNA duplex (the stem-duplex 124). Similarly, the target complementary region 120 and nucleotide clamp region 122 (if present) form a DNA/RNA duplex (the target/probe duplex 182, 184) with the target RNA. The stem-duplex 124 and target/probe duplex 182, 184 thus form a concatenated DNA/RNA duplex with a single nick at the site designated by arrow 190 (a nick is a missing phosphodiester bond (i.e. a break) between adjacent nucleotides in a double stranded polynucleotide, e.g. the RNA/DNA duplex). The site indicated by arrow 190 is adjacent the terminal nucleotide of the target RNA 120 adjacent the stem-duplex 124. The site indicated by arrow 190 also is adjacent the terminal nucleotide of the RNA hairpin extension domain 114 adjacent the target RNA 120. Thus, the nick is defined by the absence of a phosphodiester bond between the terminal nucleotide of the target RNA 120 (adjacent the stem-duplex 124) and the terminal nucleotide of the RNA hairpin extension domain 114 (adjacent the target RNA 120).

Without being bound to any particular theory with regard to the present invention, it is expected that the terminal nucleotides of the target RNA 180 and the RNA hairpin extension domain 114 adopt a conformation in which the bases are stacked; i.e. the base of the terminal nucleotide of the target RNA 180 and the base of the terminal nucleotide of the RNA hairpin extension domain 114 are adjacent each other and are in a stacked conformation with respect to each other. The base-stacked conformation provides an energetically stable conformation that is more stable than an unstacked conformation, thus the RNA hairpin extension domain 114 increases the stability of the target/probe duplex. Stacking and its effect on duplex stability are discussed in Liu et al (Nanobiology 1999; 4: 257-262), Walter et al (Proc. Natl. Acad. Sci. 1994 91:9218-9222) and Schneider et al (J. Biomol. Struct. Dyn. 2000 18:345-52), as well as many other references. As well as stabilizing the binding of target RNA that has a terminal nucleotide adjacent a terminal nucleotide of the RNA hairpin extension domain, this configuration may serve to destabilize or obstruct binding by any polynucleotide species (e.g. other than the target RNA, e.g. pre-miRNA, pri-miRNA, messenger RNA, other long transcripts) having a sequence similar to the target RNA but which are longer and have additional sequence beyond the normal end of the target RNA.

In particular embodiments of methods of performing an array analysis on a sample, illustrated by FIG. 4 at the feature 112, the target RNA 180 bound to the probes 108 at feature 112 has been modified to include a target nucleotide clamp region 186. The target nucleotide clamp region 186 of the target RNA 180 is complementary to and specifically binds to the nucleotide clamp region 122 of the probe 108. Typically, an array will include either probes (such as 106) that lack the nucleotide clamp region 122 or probes (such as 108) that include the nucleotide clamp region 122, but not both. However, in certain embodiments, an array may include probes (such as 106) that lack the nucleotide clamp region 122 and also include probes (such as 108) that include the nucleotide clamp region 122.

In typical embodiments without a nucleotide clamp region, as shown at feature 110 in FIG. 4, the terminal-most nucleotides of the target RNA 180 are capable of base-pairing with the terminal-most nucleotides of the target complementary region 120 adjacent the stem-complementary region 118. Similarly, the terminal-most nucleotides of the stem-complementary region 118 adjacent the target complementary region 120 are capable of base-pairing with the terminal-most nucleotides of the RNA hairpin extension domain 114. "Terminal-most nucleotides" references the nucleotides at an end (e.g. the 3' or 5' end) of a polynucleotide or at an end (e.g. the 3' or 5' end) of an indicated region of a probe (e.g. the target complementary region or the stem-complementary region); the "terminal-most nucleotides" generally includes at least 2 (e.g. at least 3, at least 4, at least 5, or more) contiguous nucleotides starting with the terminal nucleotide.

In typical embodiments having a nucleotide clamp region, as shown at feature 112 in FIG. 4, the terminal-most nucleotides of the target RNA 180 are capable of base-pairing with the terminal-most nucleotides of the target complementary region 120 adjacent the nucleotide clamp region 122. Similarly, the terminal-most nucleotides of the stem-complementary region 118 adjacent the nucleotide clamp region 122 are capable of base-pairing with the terminal-most nucleotides of the RNA hairpin extension domain 114.

In typical embodiments without a nucleotide clamp region, the terminal-most nucleotides of the target RNA 180 are strictly complementary to the terminal-most nucleotides of the target complementary region 120 adjacent the stem-complementary region 118. Similarly, in some such embodiments, the terminal-most nucleotides of the stem-complementary region 118 adjacent the target complementary region 120 are strictly complementary to the terminal-most nucleotides of the RNA hairpin extension domain 114.

In typical embodiments having a nucleotide clamp region 122, the terminal-most nucleotides of the target RNA 180 are strictly complementary to the terminal-most nucleotides of the target complementary region 120 adjacent the nucleotide clamp region 122. Similarly, in some such embodiments, the terminal-most nucleotides of the stem-complementary region 118 adjacent the nucleotide clamp region 122 are strictly complementary to the terminal-most nucleotides of the RNA hairpin extension domain 114.

The subject invention provides methods of analyzing a sample for target RNA, e.g. assessing for the presence or amount of a small RNA such as a miRNA. In general, the subject methods include: a) contacting an array with the sample, and b) interrogating the array to assess the amount of the target RNA in the sample. The array has a set of probes (such as described herein) bound to an array support. Each probe of the set of probes has a target complementary region bound to the array support and an RNA hairpin extension domain bound to the array support via the target complementary region. The target complementary region of each probe of the set is directed to a target RNA of interest, such as a small RNA. The array is typically contacted with the sample under specific binding conditions, e.g. stringent assay conditions. Interrogating the array typically involves detecting the presence of any detectable label associated with the probes, thereby evaluating the amount of the respective target RNAs, e.g. small RNAs such as miRNAs, in the sample.

The sample of RNA may be obtained from any source capable of providing RNA. For example, the sample of RNA may be any RNA sample, typically a sample containing RNA that has been isolated from a biological source, e.g. any plant, animal, yeast, bacterial, or viral source, or a non-biological source, e.g. chemically synthesized. The sample may already be in solution form or may be a dried sample of RNA to which a reconstitution buffer is added. In particular embodiments, the sample of RNA includes one or more small RNAs, such as e.g. short interfering RNAs (siRNAs), microRNAs (miRNA), tiny non-coding RNAs (tncRNA) and small modulatory RNA (smRNA). See Novina et al., Nature (2004) 430: 161-164. In particular embodiments, the sample includes isolated small RNAs, e.g. the sample results from an isolation protocol for small RNA such as one or more of those listed in this paragraph. In certain embodiments, the small RNA targets may include isolated miRNAs, such as those described in the literature and in the public database accessible via the at the world-wide website of the Sanger Institute (Cambridge, UK) (which may be accessed by typing "www" followed by ".sanger.ac.uk/cgi-bin/Rfam/mirna/browse.pl" into the address bar of a typical internet browser). Methods for preparing samples of miRNAs from cells are well known in the art (see, e.g., Lagos-Quintana et al, Science 294:853-858 (2001); Grad et al, Mol Cell 11:1253-1263 (2003); Mourelatos et al, Genes Dev 16:720-728 (2002); Lagos-Quintana et al, Curr Biol 12:735-739 (2002); Lagos-Quintana et al, RNA 9:175-179 (2003) and other references cited above). In some embodiments, the sample of RNA may be a whole RNA fraction isolated from a biological source and includes messenger RNA and small RNA. Such samples including a diverse set of RNAs, such as a whole RNA fraction, may be referenced herein as "complex" RNA samples.

In particular embodiments of a method in accordance with the present invention, the method includes obtaining an initial mixture containing RNA and separating components in the initial mixture based on the molecular size of the components. In certain embodiments, the method includes isolating small RNAs, especially RNAs less than about 300 bases long, e.g. less than about 200 bases long, less than about 100 bases long, or less than about 50 bases long. The size-fractionation of the initial mixture containing RNA thus provides an isolated RNA sample that includes isolated small RNAs, e.g. RNAs less than about 300 bases long (e.g. less than about 200 bases long, less than about 100 bases long, less than about 50 bases long). Any fractionation method capable of providing the isolated RNA sample may be employed. Typical methods of fractionating mixtures of polynucleotides according to size are known and need not be described in detail here. In particular embodiments, a size-based separation of the sample is performed by contacting the sample with a size fractionation medium under denaturing conditions and recovering a fraction containing the small RNAs that are of interest; such a method is described in a U.S. patent application Ser. No. 11/264,783, filed by Wang on Oct. 31, 2005.

In various embodiments, at least about 10% (e.g. at least about 20%, 40% or 60%) of the RNAs in the sample are shorter than about 300 bases, e.g. generally shorter than about 200 bases, shorter than about 100 bases. This percentage is calculated as: (mass of RNAs less than about 300 (or less than about 200, or less than about 100) bases long in a given volume of the sample comprising the small RNAs) divided by (total mass of RNA in the given volume of the sample comprising the small RNAs), and then expressed as a percentage.

In certain embodiments, long polynucleotides constitute less than about 80% (e.g. less than about 60%, less than about 40%, less than about 20%, less than about 10%) of the total polynucleotides in the sample. This percentage is calculated as: (mass of long polynucleotides in a given volume of the sample) divided by (total mass of polynucleotides in the given volume of the sample), and then expressed as a percentage. In certain embodiments, long polynucleotides (e.g. polynucleotides longer than about 300 bases, longer than about 400 bases, longer than about 500 bases) make up an insubstantial amount of the sample. In this regard, "an insubstantial amount" is an amount which does not substantially interfere with binding of small RNAs to the probes of the array, i.e. less than about 5% error is introduced into the binding measurements obtained during interrogation of the array due to the presence of the long polynucleotides.

In particular embodiments, the RNA in the sample is labeled prior to being contacted with the array. In certain embodiments, the sample may be isolated from a source already labeled. In typical embodiments, binding of labeled small RNAs to the probes of the array is detected by detecting the label associated with the probes (due to binding of the labeled small RNAs). In general, labeling methods are well known in the art (e.g., using RNA ligase, polyA polymerase, terminal transferase, or by labeling the RNA backbone, etc.; see, e.g., Ausubel, et al., Short Protocols in Molecular Biology, 3rd ed., Wiley & Sons 1995 and Sambrook et al., Molecular Cloning: A Laboratory Manual, Third Edition, 2001 Cold Spring Harbor, N.Y.), and, accordingly, such methods do not need to be described here in great detail. The observable label may be any observable label known in the art, e.g. a chromophore, a fluorescent label, a spin label, a radioisotope label, a mass label, a sequence label, a chemically reactive tag, an affinity label, or any other known label. In particular embodiments, the label is a fluorescent dye, which labels will be described in greater detail below.

Fluorescent dyes of particular interest include: xanthene dyes, e.g. fluorescein and rhodamine dyes, such as fluorescein isothiocyanate (FITC), 6 carboxyfluorescein (commonly known by the abbreviations FAM and F), 6 carboxy-2',4',7',4,7-hexachlorofluorescein (HEX), 6 carboxy 4',5' dichloro 2',7' dimethoxyfluorescein (JOE or J), N,N,N',N' tetramethyl 6 carboxyrhodamine (TAMRA or T), 6 carboxy X rhodamine (ROX or R), 5 carboxyrhodamine 6G (R6G5 or G5), 6 carboxyrhodamine 6G (R6G6 or G6), and rhodamine 110; cyanine dyes, e.g. Cy3, Cy5 and Cy7 dyes; Alexa dyes, e.g. Alexa-fluor-555; coumarins, e.g. umbelliferone; benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, e.g. cyanine dyes such as Cy3, Cy5, etc; BODIPY dyes and quinoline dyes. Specific fluorophores of interest that are commonly used in subject applications include: Pyrene, Coumarin, Diethylaminocoumarin, FAM, Fluorescein Chlorotriazinyl, Fluorescein, R110, Eosin, JOE, R6G, Tetramethylrhodamine, TAMRA, Lissamine, ROX, Napthofluorescein, Texas Red, Napthofluorescein, Cy3, and Cy5, etc. More information about commercially available dyes for oligonucleotide conjugation can be found at the Synthegen website (which may be accessed by typing "www" followed by ".synthegen.com" into the address bar of a typical internet browser). Any such dyes may potentially be used in accordance with the methods described herein. Such labels typically are well known in the art.

In embodiments in which a probe containing a nucleotide clamp is employed, the RNA in a sample may be extended to add nucleotides that are complementary to the nucleotide clamp of the probe. The addition of the nucleotides to the RNA in the sample may be done before, simultaneously with or after labeling. In representative embodiments, a mononucleotide, di-nucleotide, tri-nucleotide, tetra-nucleotide or penta-nucleotide moiety is added to either the 3' or the 5' ends of the RNA of a sample using an enzyme, e.g., an RNA or DNA ligase or terminal transferase. A variety of RNA and DNA ligases may be purchased from a variety of vendors (e.g., Pharmacia, Piscataway, N.J.; New England Biolabs, Beverly, Mass.; and Roche Diagnostics, Indianapolis, Ind.) and employed according to the instructions supplied therewith. In an embodiment of particular interest, the nucleotide(s) added to the RNA are covalently linked to a label, e.g., a fluorophore, such that the RNA is labeled by the addition of the fluorescent nucleotide. Labeled mononucleotides, di-nucleotides, tri-nucleotides, tetra-nucleotides, penta-nucleotides or higher order labeled polynucleotides are termed "nucleotide label moieties" herein. Nucleotide clamps are further described in U.S. patent application Ser. No. 11/173,693, filed by Wang on Jul. 1, 2005. Labeling methods are further described in U.S. patent application Ser. No. 11/048,225, filed by Wang on Jan. 31, 2005.

In certain embodiments, binding of labeled target RNAs is assessed with respect to binding of at least one labeled control sample. In one example, a suitable labeled control sample may be made from a control cell population. In certain embodiments, a sample and a control sample may be prepared and labeled, and relative binding of the labeled target RNAs from the samples to probes on an array may be assessed. Typically, the labeled target RNAs are contacted with the array under stringent hybridization conditions.

In practicing the subject methods, the sample and control sample may be labeled to provide at least two different populations of labeled target RNAs that are to be compared. The populations of target RNAs may be labeled with the same label or different labels, depending on the actual assay protocol employed. For example, where each population is to be contacted with different but identical arrays, each population of target RNAs may be labeled with the same label. Alternatively, where both populations are to be simultaneously contacted with a single array of surface-bound probes, i.e., co-hybridized to the same array of immobilized probes, the two different populations are generally distinguishably labeled with respect to each other.

The samples are sometimes labeled using "distinguishable" labels in that the labels that can be independently detected and measured, even when the labels are mixed. In other words, the amounts of label present (e.g., the amount of fluorescence) for each of the labels are separately determinable, even when the labels are co-located (e.g., in the same tube or in the same duplex molecule or in the same feature of an array). Suitable distinguishable fluorescent label pairs useful in the subject methods include Cy-3 and Cy-5 (Amersham Inc., Piscataway, N.J.), Quasar 570 and Quasar 670 (Biosearch Technology, Novato Calif.), Alexafluor555 and Alexafluor647 (Molecular Probes, Eugene, Oreg.), BODIPY V-1002 and BODIPY V1005 (Molecular Probes, Eugene, Oreg.), POPO-3 and TOTO-3 (Molecular Probes, Eugene, Oreg.), fluorescein and Texas red (Dupont, Boston Mass.) and POPRO3 and TOPRO3 (Molecular Probes, Eugene, Oreg.). Further suitable distinguishable detectable labels may be described in Kricka et al. (Ann. Clin. Biochem. 39:114-29, 2002).

In certain embodiments, at least a first population of target RNAs and a second population of target RNAs are produced from two different target RNA-containing samples, e.g., two populations of cells. As indicated above, depending on the particular assay protocol (e.g., whether both populations are to be hybridized simultaneously to a single array or whether each population is to be hybridized to two different but substantially identical, if not identical, arrays) the populations may be labeled with the same or different labels. As such, a feature of certain embodiments is that the different populations of target RNAs are labeled with the same label such that they are not distinguishably labeled. In yet other embodiments, a feature of certain embodiments is that the different populations of target RNAs are labeled with different labels such that they are distinguishable from each other.

Accordingly, in typical embodiments the subject methods include a hybridization assay that typically includes the following: (1) providing an array having a set of probes as described herein disposed on an array support; (2) contacting a sample containing target RNAs (e.g. labeled small RNAs) with the array, under conditions sufficient to provide for specific binding, e.g. typically under stringent hybridization conditions; (3) washing the array to remove nucleic acids not bound to the array during the hybridization; and (4) detecting the hybridized target RNAs. The reagents used in each of these steps and their conditions for use may vary depending on the particular application.

The array includes an array support and a set of probes bound to the surface of the support. In particular embodiments, a set of probes includes at least five probes such as described above ("subject probes"), wherein all of said at least five probes have the same RNA hairpin extension domain and each of said at least five probes has a different target complementary region. In some embodiments, a set of probes includes at least 10 subject probes, at least 20 subject probes, at least 50 subject probes, at least 100 subject probes, at least 200 subject probes, or more subject probes, such as up to 1000 subject probes, up to 2000 subject probes, or even more subject probes. In certain embodiments, all of the subject probes have the same RNA hairpin extension domain, and each of the subject probes has different target complementary region. Each probe of the probe set may include a linker and/or stem-complementary region, as described above with regard to FIG. 1.

As indicated above, hybridization is carried out under suitable hybridization conditions, which may vary in stringency as desired; typical conditions are sufficient to produce probe/target complexes on an array surface between complementary binding members, e.g., between surface-bound probes and labeled complementary target RNAs. In certain embodiments, stringent hybridization conditions may be employed. Representative stringent hybridization conditions that may be employed in these embodiments are provided above.

In typical embodiments, after a labeling reaction to label target RNAs, the sample containing the target RNAs is contacted with an array. The conditions employed during the hybridization are sufficient to result in hybridization of the target RNAs to the probes that are directed to the target RNAs, e.g., in a buffer containing 50% formamide, 5×SSC and 1% SDS at 42° C., or in a buffer containing 5×SSC and 1% SDS at 65° C., both with a wash of 0.2×SSC and 0.1% SDS at 65° C., for example.

The above hybridization step may include agitation of the array and the sample containing the labeled target RNAs, where the agitation may be accomplished using any convenient protocol, e.g., shaking, rotating, spinning, and the like.

Standard hybridization techniques (e.g. under conditions sufficient to provide for specific binding of target RNA, e.g. target miRNAs, to the probes on the array) are used for contacting the sample with the array. Suitable methods are described in many references (e.g., Kallioniemi et al., Science 258:818-821 (1992) and WO 93/18186). Several guides to general techniques are available, e.g., Tijssen, Hybridization with Nucleic Acid Probes, Parts I and II (Elsevier, Amsterdam 1993). For descriptions of techniques suitable for in situ hybridizations, see Gall et al. Meth. Enzymol., 21:470-480 (1981); and Angerer et al. in Genetic Engineering: Principles and Methods (Setlow and Hollaender, Eds.) Vol. 7, pgs 43-65 (Plenum Press, New York 1985). See also U.S. Pat. Nos. 6,335,167; 6,197,501; 5,830,645; and 5,665,549; the disclosures of which are herein incorporated by reference. The hybridization is typically performed under stringent hybridization conditions, as described herein and as known in the art. Selection of appropriate conditions, including temperature, salt concentration, polynucleotide concentration, time (duration) of hybridization, stringency of washing conditions, and the like will depend on experimental design, including source of sample, identity of probes, degree of complementarity expected, etc., and may be determined as a matter of routine experimentation for those of ordinary skill in the art.

Following hybridization, the array is typically washed to remove unbound nucleic acids. Washing may be performed using any convenient washing protocol, where the washing conditions are typically stringent, as described above.

Following hybridization and washing, as described above, the hybridization of target analytes (e.g. RNA) to the probes is then detected using standard techniques of reading the array, i.e. the array is interrogated. Reading the resultant hybridized array may be accomplished by illuminating the array and reading the location and intensity of resulting fluorescence at each feature of the array to detect any binding complexes (e.g. probe/target duplexes) on the surface of the array. For example, a scanner may be used for this purpose that is similar to the AGILENT MICROARRAY SCANNER available from Agilent Technologies, Palo Alto, Calif. Other suitable devices and methods are described in U.S. Pat. No. 6,756,202 and U.S. Pat. No. 6,406,849. However, arrays may be read by any other method or apparatus than the foregoing, with other reading methods including other optical techniques (for example, detecting chemiluminescent or electroluminescent labels) or electrical techniques (where each feature is provided with an electrode to detect hybridization at that feature in a manner disclosed in U.S. Pat. No. 6,221,583 and elsewhere). In the case of indirect labeling, subsequent treatment of the array with the appropriate reagents may be employed to enable reading of the array. Some methods of detection, such as surface plasmon resonance, do not require any labeling of nucleic acids, and are suitable for some embodiments.

Results from interrogating the array may be raw results (such as fluorescence intensity readings for each feature in one or more color channels) or may be processed results (such as those obtained by subtracting a background measurement, or by rejecting a reading for a feature which is below a predetermined threshold, normalizing the results, calculating log ratios for the results, and/or forming conclusions based on the pattern read from the array (such as whether or not a particular target RNA may have been present in the sample, or whether or not a pattern indicates a particular condition of an organism from which the sample came).

By "normalization" is meant that data corresponding to two populations of polynucleotides (e.g. RNAs) are globally normalized to each other, and/or normalized to data obtained from controls (e.g., internal controls produce data that are predicted to be equal in value in all of the data groups). Normalization generally involves multiplying each numerical value for one data group by a value that allows the direct comparison of those amounts to amounts in a second data group. Several normalization strategies have been described (Quackenbush et al, Nat. Genet. 32 Suppl:496-501, 2002, Bilban et al Curr Issues Mol. Biol. 4:57-64, 2002, Finkelstein et al, Plant Mol. Biol. 48(1-2):119-31, 2002, and Hegde et al, Biotechniques. 29:548-554, 2000). Specific examples of normalization suitable for use in the subject methods include linear normalization methods, non-linear normalization methods, e.g., using lowest local regression to paired data as a function of signal intensity, signal-dependent non-linear normalization, qspline normalization and spatial normalization, as described in Workman et al., (Genome Biol. 2002 3, 1-16). In certain embodiments, the numerical value associated with a feature signal is converted into a log number, either before or after normalization occurs. Data may be normalized to data obtained using a support-bound polynucleotide capture agent directed to a particular control polynucleotide, where the control polynucleotide is included in the hybridization at a known concentration, for example.

In certain embodiments, results from interrogating the array are used to assess the level of binding of the target RNAs from the sample to probes on the array. The term "level of binding" means any assessment of binding (e.g. a quantitative or qualitative, relative or absolute assessment), usually done, as is known in the art, by detecting signal (i.e., pixel brightness) from a label associated with the RNA hybridized to a probe, e.g. the sample is labeled. The level of binding of labeled RNA to probe is typically obtained by measuring the surface density of the bound label (or of a signal resulting from the label).

Accordingly, since the arrays used in the subject assays may contain probes for a plurality of different target RNAs, e.g. small RNAs, the presence of a plurality of different target RNAs in a sample may be assessed. The subject methods are therefore suitable for simultaneous assessment of a plurality of target RNAs in a sample.

In certain embodiments, a surface-bound probe may be assessed by evaluating its binding to two populations of target RNAs that are distinguishably labeled. In these embodiments, for a single surface-bound probe of interest, the results obtained from hybridization with a first population of labeled target RNAs may be compared to results obtained from hybridization with the second population of target RNAs, usually after normalization of the data. The results may be expressed using any convenient means, e.g., as a number or numerical ratio, etc.

Accordingly, in typical embodiments a sample containing target RNA (e.g. isolated small RNA) is labeled, e.g. with Cy5 or Cy3, and hybridized onto an array as follows: The sample containing the target RNA is desalted (e.g. with BioRad MICRO BIO-SPIN™-6 columns, as directed by BioRad instructions) to remove excess observable label remaining from the labeling reaction. The desalted sample containing the target RNA is added to solution containing water and carrier (25-mer DNA with random sequence). The resulting solution is heated at about 100° C. for approximately 1 minute per 10 microliters of solution, and then immediately cooled on ice. The cooled solution is then added to hybridization buffer and mixed carefully. The final solution is then contacted with the array, e.g. in a SUREHYB™ hybridization chamber (Agilent Part Number: G2534A), and placed on the rotisserie of a hybridization oven overnight. The hybridization temperature is typically in the range from about 50° C. to about 65° C., or in the range from about 55° C. to about 60° C., although temperatures outside this range (e.g. in the range from about 30° C. to about 65° C., or in the range from about 45° C. to about 65° C.) may be used depending on the other experimental parameters, e.g. hybridization buffer composition and wash conditions. After the hybridization is complete, the array is washed thoroughly and dried with nitrogen as needed. The array is scanned (e.g. with an Agilent Scanner, Agilent Product Number: G2565BA). The data is then evaluated (e.g. using Agilent Feature Extraction Software, Agilent Product Number: G2567AA) for hybridization efficiency and specificity. Data may be further analyzed, e.g. using Spotfire software and Microsoft Excel.

Also provided by the subject invention are kits for practicing the subject methods, as described above. The subject kits contain at least a subject probe. The probe may be bound to the surface of a solid support and may be present in an array. The kit may also contain reagents for isolating RNA, e.g. small RNA, from a cell, reagents for labeling the RNA, reagents for hybridizing labeled RNAs to an array, a control RNA, etc. The various components of the kit may be present in separate containers or certain compatible components may be precombined into a single container, as desired.

In addition to above-mentioned components, the subject kits may further include instructions for using the components of the kit to practice the subject methods, i.e., to instructions for sample analysis. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, this means for obtaining the instructions is recorded on a suitable substrate.

The subject methods may be employed in a variety of diagnostic, drug discovery, and research applications that include, but are not limited to, diagnosis or monitoring of a disease or condition (where the expression of a particular target RNA is a marker for the disease or condition), discovery of drug targets (where the target RNA is differentially expressed in a disease or condition and may be targeted for drug therapy), drug screening (where the effects of a drug are monitored by assessing the level of a target RNA), determining drug susceptibility (where drug susceptibility is associated with a particular profile of target RNAs) and basic research (where is it desirable to identify the presence of target RNAs in a sample, or, in certain embodiments, the relative levels of a particular target RNA in two or more samples).

In certain embodiments, relative levels of target RNA (e.g. small RNAs such as miRNAs) in two or more different samples may be obtained using the above methods, and compared. In these embodiments, the results obtained from the above-described methods are usually normalized to the total amount of RNA in the sample or to control RNAs (e.g., constitutive RNAs), and compared. This may be done by comparing ratios, or by any other means. In particular embodiments, the target RNA profiles of two or more different samples may be compared to identify target RNA that are associated with a particular disease or condition (e.g., a target RNA that that is induced by the disease or condition and therefore may be part of a signal transduction pathway implicated in that disease or condition).

The practice of the present invention will employ, unless otherwise indicated, conventional techniques of synthetic organic chemistry, biochemistry, molecular biology, and the like, which are within the skill of the art. Such techniques are explained fully in the literature. Unless otherwise defined herein, all technical and scientific terms used herein have the same meaning as commonly understood by one of ordinary skill in the art to which the invention belongs. The description herein is put forth so as to provide those of ordinary skill in the art with a complete disclosure of the methods and compositions disclosed and claimed herein. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric. Standard temperature and pressure are defined as 20° C. and 1 atmosphere.

While the foregoing embodiments of the invention have been set forth in considerable detail for the purpose of making a complete disclosure of the invention, it will be apparent to those of skill in the art that numerous changes may be made in such details without departing from the spirit and the principles of the invention. Accordingly, the invention should be limited only by the following claims.

All patents, patent applications, and publications mentioned herein are hereby incorporated by reference in their entireties, provided that, if there is a conflict in definitions, the definitions provided herein shall control.

What is claimed is:

1. A probe set for detecting a target polynucleotide, comprising:
   a) a first oligonucleotide bound to a surface of a solid support by its 3' end and comprises:
      i) a surface-proximal target complementary region that base-pairs with said target polynucleotide to form a probe/target duplex; and
      ii) a surface-distal stem-complementary region; and
   b) a second oligonucleotide comprising a loop region and a stem region, wherein said stem region is complementary to said stem-complementary region,
   wherein hybridization of said first oligonucleotide and said second oligonucleotide results in a stem-loop in which the 3' terminal nucleotide of said second oligonucleotide is directly adjacent to the 5' terminal nucleotide of said first oligonucleotide, wherein said stem-loop stabilizes said probe/target duplex.

2. The probe set of claim 1, wherein said target polynucleotide is a small RNA selected from the group consisting of a short interfering RNA (siRNA), microRNA (miRNA), tiny non-coding RNA (tncRNA) and a small modulatory RNA (smRNA).

3. The probe set of claim 1, wherein said first oligonucleotide further comprises a nucleotide clamp region between the target complementary region and the stem-complementary region.

4. The probe set of claim 3, wherein said nucleotide clamp region base-pairs with a nucleotide label moiety present at a 3' end of said target polynucleotide.

5. The probe set of claim 3, wherein the target complementary region is from 10 to 25 nucleotides long.

6. The probe set of claim 1, wherein said stem-loop provides for steno hindrance for nontarget polynucleotides.

7. The probe set of claim 1, wherein said second oligonucleotide is from 15 to 50 nucleotides long.

8. An array comprising:
   a) a solid support having a surface; and
   b) at least one probe set of claim 1 bound to said surface.

9. The array of claim 8, wherein said array comprises at least 100 different features, each feature having a different probe set according to claim 1.

10. The array of claim 8, wherein said at least one probe set comprises a linker between said target complementary region and said surface.

11. A kit for assessing target polynucleotides in a polynucleotide sample, the kit comprising:
    a probe set according to claim 1; and
    one or more components selected from the group consisting of instructions for using said probe set to assess target polynucleotides in a sample; control polynucleotides; reagents for isolating target polynucleotides from a cell; and reagents for labeling said target polynucleotides.

12. A method, comprising:
    labeling a sample containing a polynucleotide to produce a labeled sample;
    contacting said labeled sample with a probe of claim 1; and
    detecting any label bound to said probe.

13. The method of claim 12, wherein said labeling comprises addition of a nucleotide label moiety to a terminus of said polynucleotide.

14. A method for evaluating small RNAs in a test sample, comprising:
    labeling the test sample containing said small RNAs to produce a sample containing labeled small RNAs;
    contacting said labeled sample with an array of claim 8; and
    detecting any label bound to said array to evaluate binding of said labeled small RNAs to said at least one probe.

15. The method of claim 14, wherein said labeling comprises addition of a nucleotide label moiety to a terminus of said small RNAs.

16. The method of claim 14, wherein said binding is evaluated relative to binding of small RNAs in a reference sample.

17. The method of claim 16, wherein said test sample and said reference samples are obtained from test and control cells, respectively.

* * * * *

UNITED STATES PATENT AND TRADEMARK OFFICE
CERTIFICATE OF CORRECTION

PATENT NO. : 7,754,475 B2
APPLICATION NO. : 11/555230
DATED : July 13, 2010
INVENTOR(S) : Hui Wang

It is certified that error appears in the above-identified patent and that said Letters Patent is hereby corrected as shown below:

Title page, Item (75), "Inventor", delete "Hul Wang," and insert -- Hui Wang, --, therefor.

In column 22, line 29, in Claim 6, delete "steno" and insert -- steric --, therefor.

Signed and Sealed this

Twenty-sixth Day of October, 2010

David J. Kappos
*Director of the United States Patent and Trademark Office*